(12) United States Patent
Longobardi

(10) Patent No.: US 10,583,012 B1
(45) Date of Patent: Mar. 10, 2020

(54) UNIVERSAL SHOULDER PROSTHESIS SYSTEM

(71) Applicant: Raphael S. F. Longobardi, Old Tappen, NJ (US)

(72) Inventor: Raphael S. F. Longobardi, Old Tappen, NJ (US)

( * ) Notice: Subject to any disclaimer, the term of this patent is extended or adjusted under 35 U.S.C. 154(b) by 0 days.

(21) Appl. No.: 16/439,639

(22) Filed: Jun. 12, 2019

Related U.S. Application Data

(60) Provisional application No. 62/728,394, filed on Sep. 7, 2018.

(51) Int. Cl.
*A61F 2/40* (2006.01)
*A61F 2/30* (2006.01)

(52) U.S. Cl.
CPC .......... *A61F 2/4014* (2013.01); *A61F 2/4059* (2013.01); *A61F 2/4081* (2013.01); *A61F 2002/30878* (2013.01); *A61F 2002/4037* (2013.01); *A61F 2220/0025* (2013.01)

(58) Field of Classification Search
CPC ........ A61F 2/40; A61F 2/4081; A61F 2/4059; A61F 2/4014; A61F 2002/30607; A61F 2002/30614; A61F 2002/30616; A61F 2002/30367; A61F 2002/30736; A61L 27/28

See application file for complete search history.

(56) References Cited

U.S. PATENT DOCUMENTS 6,783,549 B1  8/2004  Stone et al.
8,007,538 B2  8/2011  Gunther
(Continued)

FOREIGN PATENT DOCUMENTS

DE  10 2006 041 550 A1  11/2007
EP  1472999 B1  3/2010

OTHER PUBLICATIONS

Ascione, Francesco, et al., "Reverse Shoulder Arthroplasty with a New Convertible Short Stem: Preliminary 2- to 4-year Follow-up Results," Journal of Shoulder and Elbow Arthroplasty, Dec. 13, 2017, vol. 1, pp. 1-9.
(Continued)

*Primary Examiner* — Brian A Dukert
(74) *Attorney, Agent, or Firm* — Cahn & Samuels, LLP

(57) ABSTRACT

A modular shoulder prosthesis system, in at least one embodiment, provides flexibility in shoulder replacements and ability to switch between a traditional anatomic Total Shoulder Replacement (ta-TSR) to a reverse Total Shoulder Replacement (r-TSR). Optionally, the system provides for a modular adaptation for the glenoid side in a Total Shoulder Replacement (TSR). The system includes a baseplate, a modular component, a humeral stem and a modular humeral component. The baseplate includes a base with a pair of notches extending down from the top surface on opposed sides of the base. The modular component and the modular humeral component configured to cooperate with each other. The baseplate is capable of attachment to different modular components and the humeral stem is capable of attachment to different modular humeral components to facilitate both ta-TSR and r-TSR with a change in the modular component and change in the modular humeral component.

24 Claims, 9 Drawing Sheets

(56) References Cited

U.S. PATENT DOCUMENTS

| | | | |
|---|---|---|---|
| 8,246,687 B2* | 8/2012 | Katrana | A61F 2/4014 623/19.13 |
| 8,968,410 B2 | 3/2015 | Veronesi et al. | |
| 9,283,075 B2 | 3/2016 | Wiley et al. | |
| 9,522,067 B2* | 12/2016 | Frankle | A61F 2/40 |
| 9,610,165 B2* | 4/2017 | Poncet | A61F 2/4014 |
| 10,064,734 B2 | 9/2018 | Burkhead, Jr. et al. | |
| 2004/0220674 A1* | 11/2004 | Pria | A61F 2/40 623/19.12 |
| 2008/0294268 A1 | 11/2008 | Baum et al. | |
| 2009/0149961 A1 | 6/2009 | Dallmann | |
| 2012/0239156 A1* | 9/2012 | De Wilde | A61B 17/1684 623/19.11 |
| 2016/0270922 A1 | 9/2016 | Pressacco et al. | |
| 2018/0064537 A1 | 3/2018 | Pressacco et al. | |
| 2018/0085226 A1* | 3/2018 | Baumgarten | A61F 2/40 |
| 2018/0103967 A1 | 4/2018 | Rouyer et al. | |
| 2018/0271669 A1 | 9/2018 | Goodman | |

OTHER PUBLICATIONS

Biomet Orthopedics, Inc., "Bio-Modular Choice Shoulder System Surgical Technique Standard and Mini Stem," 2008, Rev. 111508, pp. 1-25.

Biomet Orthopedics, Inc., "Bio-Modular Shoulder System Reverse Conversion Option," 2011, Rev. 021511, pp. 1-2.

Biomet Orthopedics, Inc., "Comprehensive Reverse Shoulder System Surgical Technique," 2015, Rev. 0715, pp. 1-60.

Group FH Ortho, "ARROW Universal Shoulder Prosthesis," Feb. 2018, pp. 1-2.

Integra LifeSciences Corp., "Integra Titan Modular Shoulder System, 2.5," 2016, pp. 1-8.

Lima Corp., "SMR Modular Shoulder Replacement SMR System Surgical Technique," Jul. 2015, pp. 1-76.

Lima Corp., "SMR Modular Should Replacement SMR System Surgical Technique," unknown date—downloaded on Nov. 10, 2018, pp. 1-68.

Musculoskeletal Key, "The SMR Shoulder System of Lima Corporate," printed Nov. 10, 2018, pp. 1-4.

Stryker Corporation, "ReUnion TSA Total Shoulder Arthroplasty System Operative technique," 2017, Rev 3, Mar. 2017, pp. 1-88.

Valenti, Philippe, et al., "Convertible Glenoid Components Facilitate Revisions to Reverse Shoulder Arthroplastry Easier: Retrospective Review of 13 Cases," The American Journal of Orthopedics, Feb. 8, 2018, vol. 47, Issue 2, pp. 1-9.

Werner, Brian C., et al., "Platform systems in shoulder arthroplasty," Musculoskeletal Medicine, Jan. 20, 2016, vol. 9, pp. 49-53.

European Patent Office, International Search Report in PCT App. No. PCT/US2019/050253, dated Jan. 7, 2020.

European Patent Office, Written Opinion in PCT App. No. PCT/US2019/050253, dated Jan. 7, 2020.

* cited by examiner

UNIVERSAL SHOULDER PROSTHESIS SYSTEM

This patent application claims priority to U.S. Patent Application No. 62/728,394 filed on Sep. 7, 2018, which is hereby incorporated by reference.

I. FIELD OF THE INVENTION

The invention relates to a modular shoulder prosthesis system that provides for flexibility in shoulder replacements and allows for a more efficient switch for a patient between a traditional anatomic Total Shoulder Replacement (ta-TSR) to a reverse Total Shoulder Replacement (r-TSR). In at least one embodiment, the system also, or alternatively, provides for a modular adaptation for the glenoid side in a Total Shoulder Replacement (TSR).

II. BACKGROUND OF THE INVENTION

TSRs have evolved over the last 70 years, with the greatest degree of its evolution occurring within the past 20 years. The understanding of the complexity of the shoulder has resulted in the ability to better treat the multiple conditions that afflict the shoulder. Glenohumeral arthritis ranges from simple to complex due to etiology and deformity. Post traumatic glenohumeral arthritis, along with the deformity of both the glenoid and humeral head present challenges for the shoulder arthroplasty surgeon. Similarly, the problem of rotator cuff deficiency and rotator cuff arthropathy has resulted in the development of treatment and prosthetic design specific to address the loss of the main motors of the shoulder.

Currently, there are two types of TSR—traditional anatomic total shoulder replacement (ta-TSR) and reverse total shoulder replacement (r-TSR). Ta-TSR utilizes resurfacing of the humeral head and glenoid in the setting of an intact and functioning rotator cuff. Glenohumeral arthritis has been treated with ta-TSR, the current gold standard being the resurfacing of the humeral head with a stemmed or metaphyseal component along with a replacement of the humeral head articular portion with a Cobalt-Chromium (Co—Cr) implant. Modularity of the humeral components allows for appropriate sizing of the head in diameter and thickness to match the resected articular surface of the patient.

To revise from the ta-TSR to r-TSR often requires removal of the glenoid component and reconstruction of the glenoid bone stock. Ta-TSR utilize all polyethylene glenoid components which become the typical point of failure for the ta-TSR. R-TSR utilizes a porous in-growth metal design with locking screws for glenoid fixation. Modularity has always centered on being able to change the humeral components from ta-TSR to r-TSR, for example, a humeral head component to a socket configuration.

The resurfacing of the glenoid has evolved over the past 70 years. Originally, polyethylene bonded to metal, also known as metal-backed glenoids, was cemented into the glenoid bone. These failed at the polyethylene-metal interface due to stresses and edge loading of the component. What evolved was the use of all polyethylene components. First, all polyethylene with a keel was used, followed by all polyethylene with multiple pegs.

There was a higher rate of failure for the cemented keeled components, so currently the gold standard for glenoid resurfacing in ta-TSR is a cemented pegged, all polyethylene component.

The most common cause of failure of the ta-TSR is due to glenoid loosening secondary to rotator cuff failure/tear. The resulting superior migration of the humeral head, with concomitant change in the center of rotation (C.O.R.) from rotator cuff failure produces edge loading of the glenoid component. This asymmetric mechanical loading results in rocking and loosening of the polyethylene prosthesis from the cement and bone of the glenoid.

R-TSR evolved from the specific abnormal mechanics of the rotator cuff deficient shoulder, as previously described. In the rotator deficient condition, the deltoid muscle becomes the predominant motor, but in an inefficient manner. The deltoid muscle contraction functions to result in "hinged abduction" of the humeral head/humeral shaft. The humeral head and greater tuberosity lever on the undersurface of the acromion and superior portion of the glenoid. Ta-TSR is contra-indicated in the setting of rotator cuff deficiency, due to the known catastrophic results to the glenoid component.

The development of the r-TSR addresses the rotator cuff deficient, painful arthritic shoulder. The design of r-TSR is to maximize deltoid fiber length to allow more efficient contraction and function of the deltoid in elevation of the arm. The prosthetic components are designed to change the C.O.R. to one that is more inferior and medial to the native joint.

The design of r-TSR has also evolved over the past 20 years. The original "Grammont" style sought to inferiorly displace the humerus to maximize deltoid fiber length; this resulted in inferior scapular notching, leading to failure. The current revised designs include a C.O.R. which is more lateral and inferior to the native C.O.R. The implant design is for an in-growth trabecular metal baseplate with locking screws to secure the component to the bony glenoid. The relatively minimally curved glenoid is replaced with a glenosphere: a solid Co—Cr semi-spherical to spherical surface that attaches to the in-growth metal base-plate. This is typically through a combination of a Morse taper fit and center screw fixation. The glenosphere is typically inserted at an inferiorly directed version angle, between 5-10 degrees. This allows for inferior offset of the humerus, elongation of the deltoid muscle fibers and a joint reactive force in line with prosthetic alignment.

R-TSR already have asymmetric, higher shear and higher loading of the glenoid component, called the glenosphere and baseplate construct. Despite these greater loads, in growth metal baseplates with locking screws are not the cause of failure, due to the excellent bone incorporation and stability.

The r-TSR has a different humeral component design as well. Where the ta-TSR has the Co—Cr humeral head, the r-TSR had the Co—Cr glenosphere attached to the glenoid. The humerus had a stemmed component but attached to the top is a polyethylene cup or humeral cup to articulate with the glenosphere. The modularity of components, specifically glenosphere sizing and humeral cup sizing, allow for multiple permutations to achieve the most successful and stable construct.

Current long-term studies on viability of r-TSR have revealed that the construct of an in-growth metal baseplate with locking screws has excellent long-term fixation without evidence of loosening, even in osteoporotic bone.

Currently, there is not a single company known to the inventor that has a universal baseplate for both ta-TSR and r-TSR. Further, the modularity that exists today allows only for conversion of a ta-TSR humeral stem to accommodate a r-TSR humeral cup. Conversion to a r-TSR requires removal of the polyethylene glenoid with reconstruction of the glenoid bone with tricortical bone, often taken from the patient's own iliac crest, and consequential donor site morbidity.

III. SUMMARY OF THE INVENTION

In at least one embodiment, a modular system will allow the surgeon to achieve either exchanges, humeral or glenoid component, without extravagant amount of equipment to be processed and secured, or more complex operative procedures to be performed. A truly versatile and modular system would allow for a baseplate to accept either a traditional anatomic glenoid component or a reverse total shoulder glenosphere, without compromising long term security and function. At least one embodiment according to the invention will allow for all of this.

The novelty of this design, in at least one embodiment, allows for a single glenoid component that can be used for traditional, anatomic TSR, primary reverse TSR and revision of anatomic to reverse TSR. In at least one embodiment, a porous metal baseplate with locking screw fixation is used for the traditional anatomic glenoid component. An all metal glenoid component composed of the typical Cobalt-Chromium (Co—Cr), which is the most current and common alloy used in joint replacement, is press-fit onto the baseplate utilizing, for example, a Morse taper central fixation peg. The smooth, Co—Cr glenoid component, in at least one embodiment, would have anterior sided flanges to assist with the removal of the component. In at least one further embodiment, the flanges will provide additional connection points between the base and the modular component.

By using the same concept for securing the ta-TSR glenoid components, this prosthetic design will diminish glenoid loosening as a reason for revision of a ta-TSR. Further, the all metal glenoid baseplate solves the issue of glenoid bone loss and glenoid deformity during primary ta-TSR. In cases of posterior glenoid bone loss, the B2 or C glenoid types, the in-growth metal baseplates can be pre-fashioned/constructed to include posterior wedges: neutral, 10 degree and 25-degree wedges to allow for complete reconstruction of the glenoid using ingrowth trabecular metal and locking screws. Regardless of glenoid bony deformity and defects, a neutral or wedge baseplate can be used for either the ta-TSR or the r-TSR in the primary condition.

If the rotator cuff failure occurs and necessitates conversion to a r-TSR, the revision is facilitated by the modularity of the already inserted baseplate and the humeral stem components. First, the dual mobility humeral head can be removed. As long as the humeral fixation of the stem is intact, a modular humeral cup can be secured to this stem as part of the conversion to a r-TSR. Second, the Co—Cr glenoid surface can be removed from the baseplate and the glenosphere can be attached without revising the baseplate. In at least one embodiment, built into the glenosphere component will be a 7 or 10-degree inferior inclination, to allow for proper tensioning of the deltoid to maximize its function.

A modular shoulder prosthesis system including a baseplate having a base with a plurality of attachment holes passing therethrough and a pair of notches on opposed sides of the base, and a central stem extending from the base and axially centered with one of the plurality of attachment holes; a modular component (for the glenoid side) configured to be removably attached to the base, the modular component having a plug for insertion into at least one attachment hole of the base; a humeral stem having a receiving cavity extending in from one face; and a modular humeral component configured to cooperate with the modular component, the modular humeral component having a post configured for removable insertion into the receiving cavity of the modular humeral component, and wherein the baseplate is capable of attachment to different modular components and the humeral stem is capable of attachment to different modular humeral components to facilitate both traditional anatomic total shoulder replacement and reverse total shoulder replacement with a change in the modular component and change in the modular humeral component. In a further embodiment, the pair of notches extend down from a mounting surface of the base.

In a further embodiment to either of the previous embodiments the modular component includes a pair of flanges extending from opposing sides of the modular component, the flanges configured to overlap with the notches when the modular component is attached to the base. In a further embodiment to the embodiment of the prior paragraph, the modular component includes a pair of flanges extending down from opposing sides of the modular component, the flanges configured to engage with an interference fit the notches when the modular component is attached to the base.

In a further embodiment to any of the previous embodiments, the plug of the modular component and/or the post of the modular humeral component include a Morse taper.

In a further embodiment to any of the previous embodiments, the modular component for a ta-TSR includes a base having a concave surface, and the plug extends from a surface opposite of the concave surface to be inserted into the glenoid. Further to the previous embodiment, the modular component includes Co—Cr. Further to the embodiments of the previous two paragraphs, the modular component for a r-TSR includes a base, a glenosphere extending from the base, and the plug extends from a surface of the base opposite the glenosphere to be inserted into the glenoid. Further to the previous embodiment, the glenosphere is approximately a three-quarters sphere or a hemi-spherical dome. Further to the previous two embodiments, the glenosphere includes Cobalt-Chromium.

In a further embodiment to any of the previous embodiments, the modular humeral component for a ta-TSR includes a base having an inner head; an outer shell over the inner head; and the post extending from the base on a surface opposing the inner head. Further to the previous embodiment, the inner head is a hemi-spherical dome and the outer shell is a hemi-spherical cap that fits over the inner head. Further to the previous two embodiments, the inner head includes Co—Cr and the outer shell includes a high-density polyethylene. In a further embodiment there is dual-mobility between the outer shell and the concave surface of the modular component attached to the glenoid. Further to the embodiments of the previous three paragraphs, the modular humeral component for a r-TSR includes a base having a receiving cavity, and the post extends from a surface of the base opposing the receiving cavity to be inserted into the humeral stem. Further to the previous embodiment, the base includes high-density polyethylene to form a concave surface in the receiving cavity or the modular humeral component further includes a shell inserted into the receiving cavity of the base. Further to the previous shell embodiment, the base includes Co—Cr and the shell includes a high-density polyethylene. The embodiments of this paragraph and the previous paragraph are used in combination where one component has a glenosphere and the other component has a concave surface.

In a further embodiment to any of the previous embodiments, the system further including a plurality of attachment mechanisms, wherein the attachment holes of the base of the baseplate are configured to engage with the attachment mechanisms. Further to the previous embodiment, the attachment mechanisms include variable angle locking screws.

Further to the embodiments of the previous three paragraphs, modular component includes a passageway through which a fastener passes to engage the respective glenoid base. Further to the embodiments of the last two paragraphs, modular humeral component has an eccentrically placed plug.

A modular shoulder prosthesis system including a baseplate having a base with a plurality of attachment holes passing therethrough and a pair of notches on opposed sides of the base, and a central stem extending from the base and axially centered with one of the plurality of attachment holes; a modular component configured to be removably attached to the base, the modular component having a plug for insertion into at least one attachment hole of the base, and wherein the baseplate is capable of attachment to different modular components to facilitate both traditional anatomic total shoulder replacement and reverse total shoulder replacement with a change in the modular component. Further to the previous embodiment, the pair of notches extend down from a mounting surface and along the sides of the base. Further to the embodiments of this paragraph, the modular component includes a pair of flanges extending from (including down from) opposing sides of the modular component, the flanges configured to overlap with the notches when the modular component is attached to the base and/or to engage with an interference fit the notches when the modular component is attached to the base.

Further to the embodiments of the previous paragraph, the plug of the modular component includes a Morse taper and/or threaded surface for engagement of the baseplate. In an alternative embodiment, the component including the plug have a passageway passing therethrough for a fastener to engage the component and/or any attachment mechanism.

Further to the embodiments of the previous two paragraphs, the modular component for a ta-TSR includes a base having a concave surface, and the plug extends from a surface opposite of the concave surface. Further to the previous embodiment, the modular component includes Co—Cr. Further to the embodiments of the previous two paragraphs, the modular component for r-TSR includes a base, a glenosphere extending from the base, and the plug extends from a surface of the base opposite the glenosphere. Further to the previous embodiment, the glenosphere is approximately a three-quarters sphere. Further to the previous two embodiments, the glenosphere includes Co—Cr.

Further to the embodiments of the previous three paragraphs, the system further including at least one attachment mechanism, wherein the attachment holes of the base of the baseplate are configured to engage with the attachment mechanism. Further to the previous embodiment, the attachment mechanisms include variable angle locking screws.

Further to the previous embodiments, the humeral stem is replaced with a second baseplate configured for attachment to the humerus. In at least one alternative embodiment, the second baseplate is larger than the glenoid baseplate.

In at least one embodiment, a modular shoulder prosthesis system including: a first baseplate configured to attach to a glenoid, the first baseplate having a base with a plurality of attachment holes passing therethrough and a pair of notches on opposed sides of the base, the pair of notches extend down from a mounting surface of the base, and a central stem extending from the base and axially centered with one of the plurality of attachment holes; a modular component configured to be removably attached to the base, the modular component having a plug for insertion into at least one attachment hole of the base; a second baseplate configured to attach to a humerus, the second baseplate having a receiving cavity extending in from one face; and a modular humeral component configured to cooperate with the modular component, the modular humeral component having a post configured for removable insertion into the receiving cavity of the second baseplate, and wherein the first baseplate is capable of attachment to different modular components and the second baseplate is capable of attachment to different modular humeral components to facilitate both traditional anatomic total shoulder replacement and reverse total shoulder replacement with a change in the modular component and change in the modular humeral component. In a further embodiment, the variously described modular components and modular humeral components of the summary section may be used in this system.

IV. BRIEF DESCRIPTION OF THE DRAWINGS

Any cross-hatching present in the figures is not intended to identify or limit the type of material present for the element shown in cross-section. In figures that include multiple elements shown in cross-section, the cross-hatching will be different directions for the different elements FIGS. 1A-1C illustrate a baseplate according to at least one embodiment of the invention. FIG. 1A illustrates a top view. FIG. 1B illustrates a side view with phantom lines illustrating the internal construction according to at least one embodiment of the invention. FIG. 1C illustrates an alternative cross-section of the baseplate for an alternative attachment with a glenosphere modular component from a view from superiorly of the glenosphere.

FIG. 2B is a cross-section taken at 2B-2B in FIG. 2A, which illustrates a top view of the modular glenoid component.

Figure 3A:
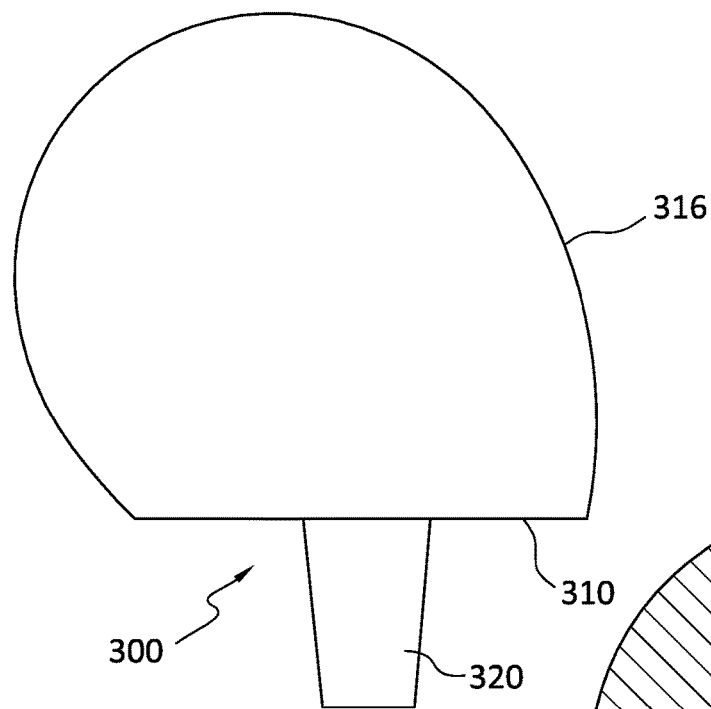
Figure 3B:
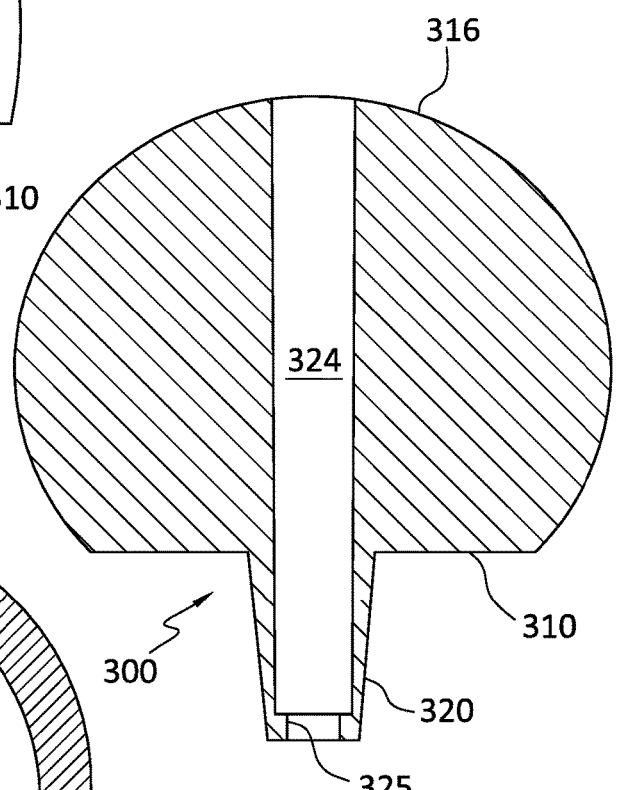
Figure 3C:
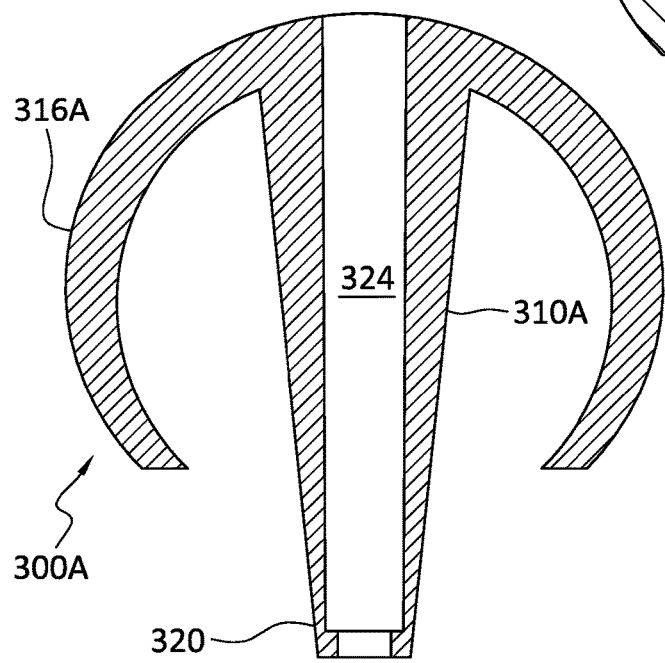

FIGS. 3A-3D illustrate a glenosphere component according to at least two embodiments of the invention. FIG. 3A illustrates a side view. FIG. 3B is a cross-section taken along a vertical plane taken at 3B, 3C-3B, 3C in FIG. 3D, which illustrates a face-on view or view from lateral shoulder view. FIG. 3C illustrates an alternative glenosphere component as a cross-section taken at 3B, 3C-3B, 3C in FIG. 3D.

Figure 3D:
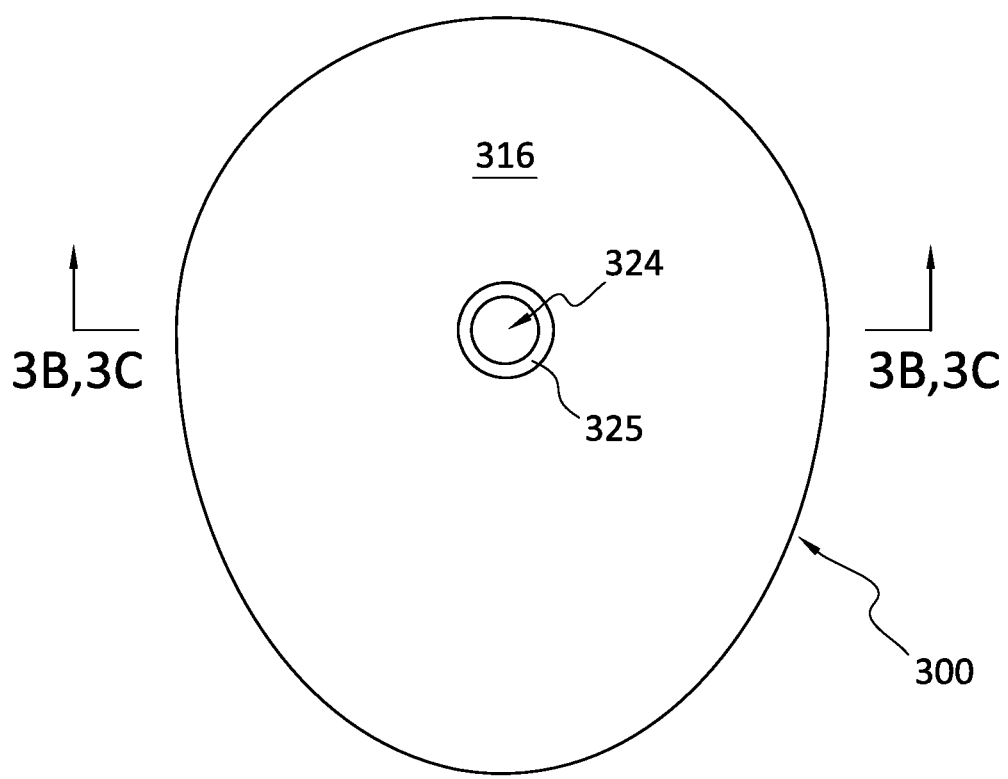
Figure 3E:
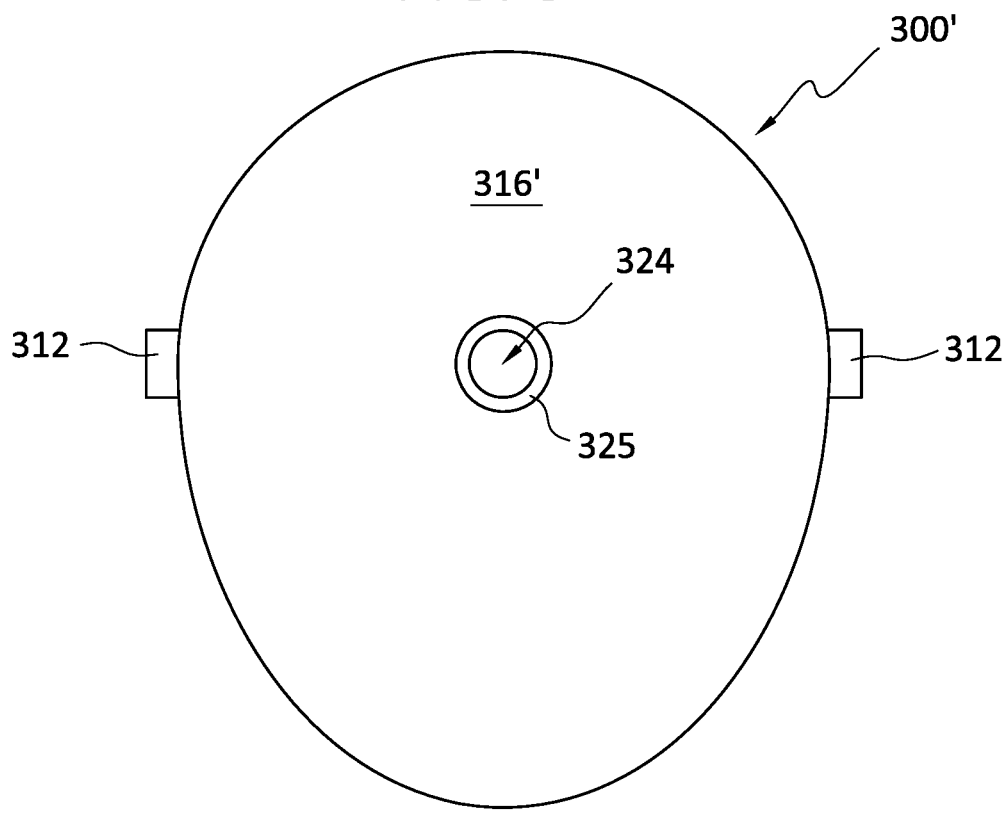

FIG. 3E illustrates a face-on view or view from lateral shoulder view of an alternative glenosphere component according to at least one embodiment of the invention.

Figure 3F:
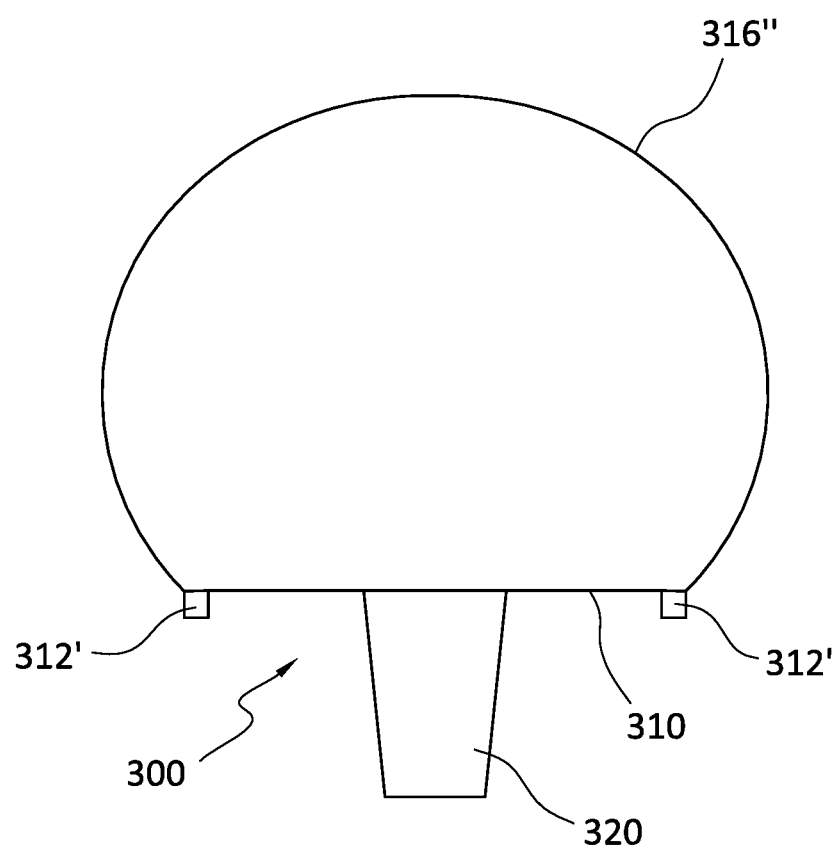

FIG. 3F illustrates a top view of another alternative glenosphere component according to at least one embodiment of the invention.

Figure 4A:
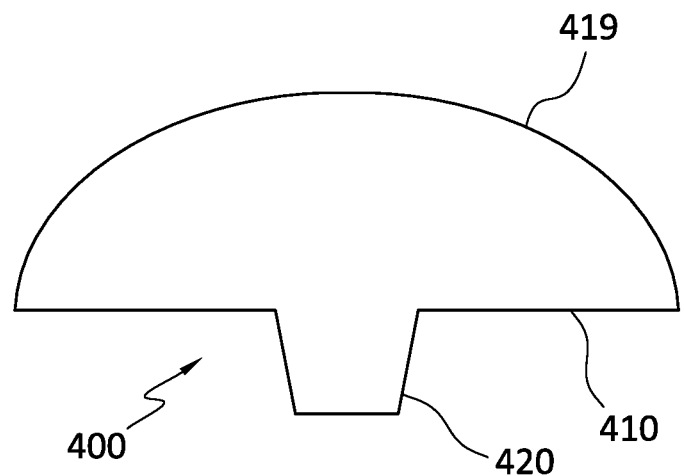
Figure 4B:
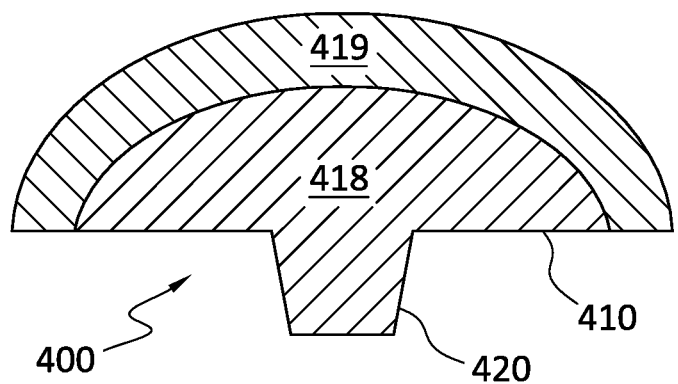

FIG. 4A illustrates a side view of a humeral head according to at least one embodiment of the invention. FIG. 4B illustrates a cross-section of the humeral head illustrated in FIG. 4A taken along a vertical plane taken through a diameter of the humeral head.

Figure 5A:
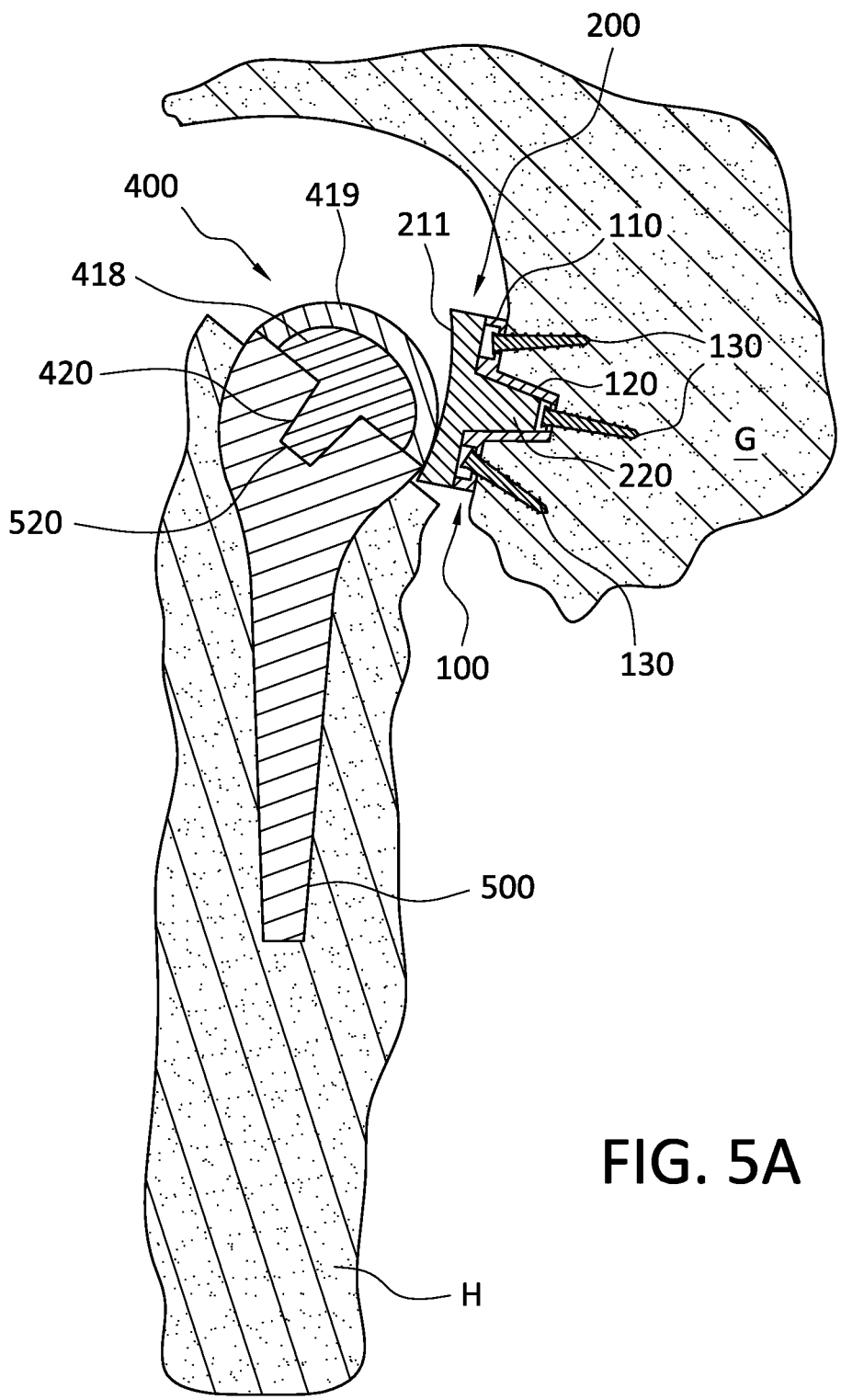
Figure 5B:
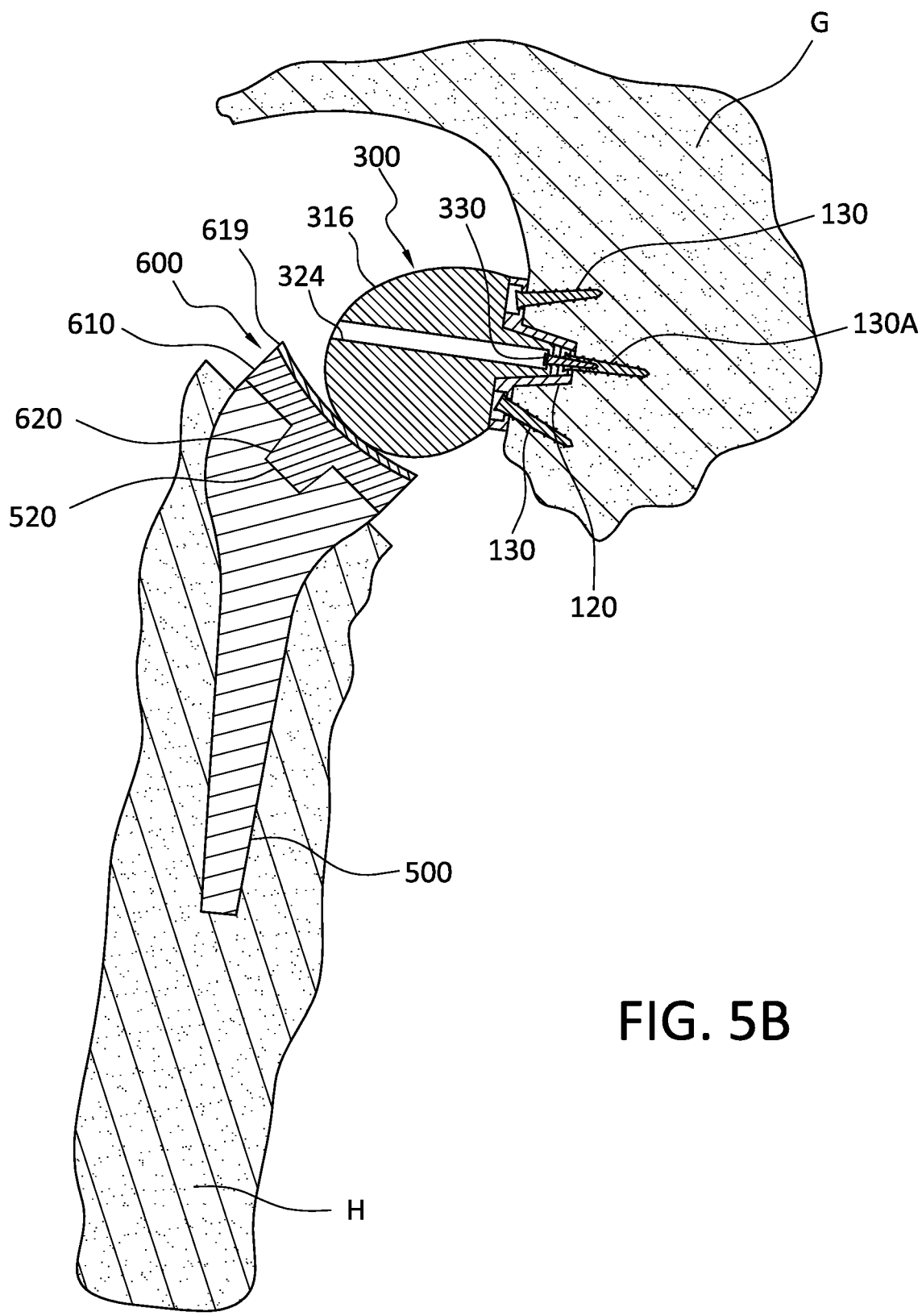

FIGS. 5A and 5B illustrate cross-sections of examples of a modular glenoid component and humeral head implanted in bone according to at least two embodiments of the invention.

Figure 6A:
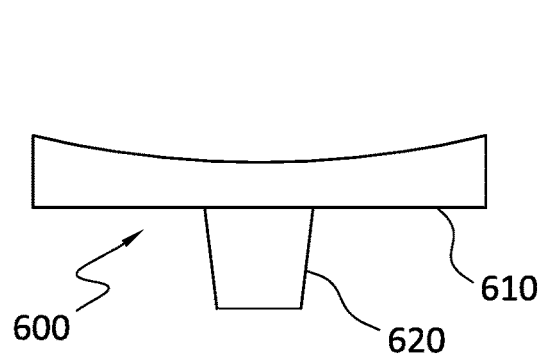
Figure 6B:
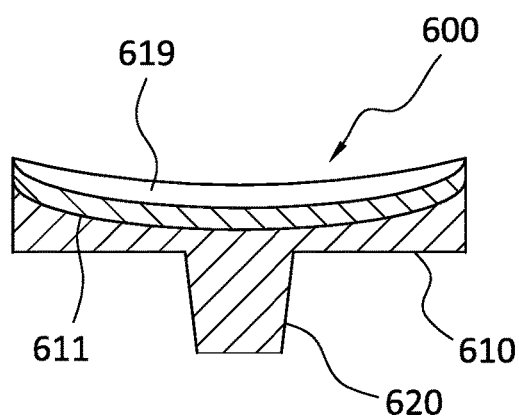

FIG. 6A illustrates a side view of a humeral cup according to at least one embodiment of the invention. FIG. 6B illustrates a cross-section of the humeral cup illustrated in FIG. 6A taken along a vertical plane taken through a diameter of the humeral cup with a shell insert according to at least one embodiment of the invention.

Figure 7A:
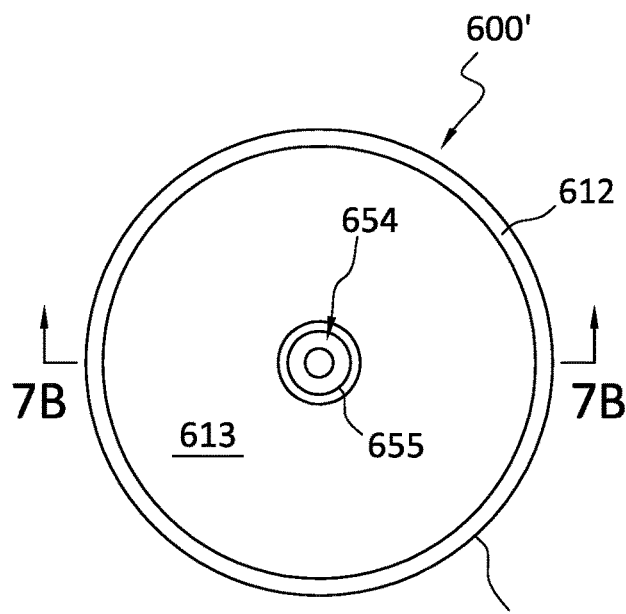
Figure 7B:
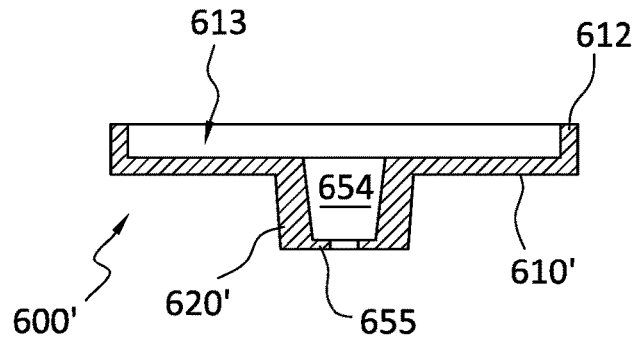
Figure 7C:
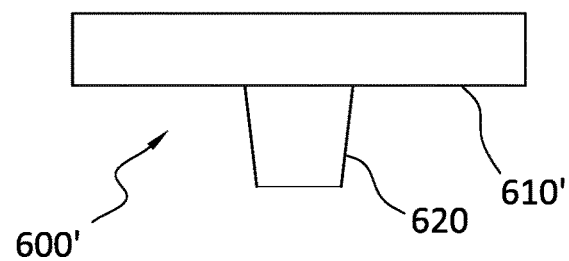

FIGS. 7A-7C illustrate an alternative humeral cup according to at least one embodiment of the invention. FIG. 7A illustrates a top view. FIG. 7B illustrates a cross-section taken at 7B-7B in FIG. 7A. FIG. 7C illustrates a side view of an alternative humeral cup according to at least one embodiment of the invention.

V. DETAILED DESCRIPTION OF THE DRAWINGS

The invention in at least one embodiment includes a modular shoulder replacement system having a glenoid baseplate configured for attachment to a patient's glenoid with at least one attachment mechanism. Examples of attachment mechanism include screws, variable angle locking screws, and an impactable central cylinder. The baseplate has a mounting surface for engagement of a modular glenoid component for a ta-TSR or a modular glenosphere component for a r-TSR. The mounting surface refers to the substantially planar surface of the baseplate opposite the glenoid. Both the modular glenoid component and the modular glenosphere component are examples of a modular component. The attachment in at least one embodiment between the modular component and the baseplate is through, for example, a Morse taper, which may be a dual threaded Morse taper that is axially located with reference to the baseplate. In an alternative embodiment with or without the Morse taper, a torque limiting fastener, such as a screw or a bolt, is used to further secure the modular glenoid component to the baseplate by engaging the baseplate and/or the central attachment mechanism anchored in the patient's glenoid. In a further embodiment, the attachment is facilitated with a threaded connection where the modular component is screwed into the baseplate.

In at least one embodiment the modular shoulder replacement system further includes a humeral stem for attachment to a patient's humeral bone. The humeral stem having a receiving socket for insertion of a post (or other connection piece) from a modular humeral head for a ta-TSR or a modular humeral cup for a r-TSR. Both the modular humeral head and the modular humeral cup are examples of a modular humeral component. In at least one embodiment, the modular humeral component is attached to the humeral stem using, for example, a Morse taper, which may be a dual threaded Morse taper. In an alternative embodiment, the system includes a mounting base that is attached to the humeral stem component on to which the modular humeral head or modular humeral cup is attached. In an alternative embodiment with or without the Morse taper, a torque limiting fastener, such as a screw or a bolt, is used to further secure the modular humeral component to the humeral stem by engaging the receiving socket. In a further embodiment, the attachment is facilitated with a threaded connection where the modular humeral component is screwed into the humeral stem. In an alternative embodiment, a baseplate used for the glenoid is adapted for use instead with the humerus in place of the humeral stem. In at least one alternative embodiment, the humeral baseplate is larger than the glenoid baseplate.

The baseplate and the humeral stem are designed to remain in place while switching the modular component and the modular humeral component, respectively, to switch from a ta-TSR to a r-TSR.

Figure 1A:
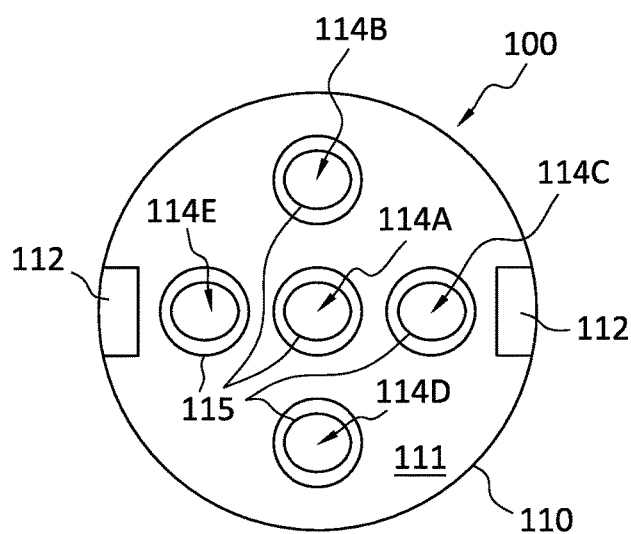
FIGS. 1D and 1E illustrate side views of alternative baseplates according to at least two embodiments of the invention.
Figure 1C:
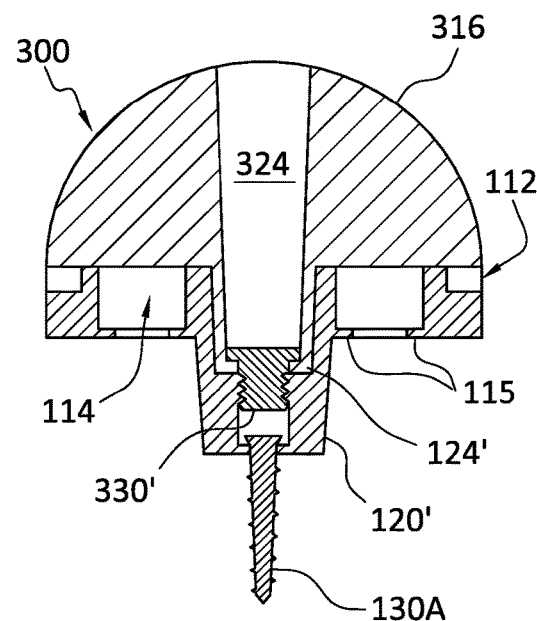
Figure 1B:
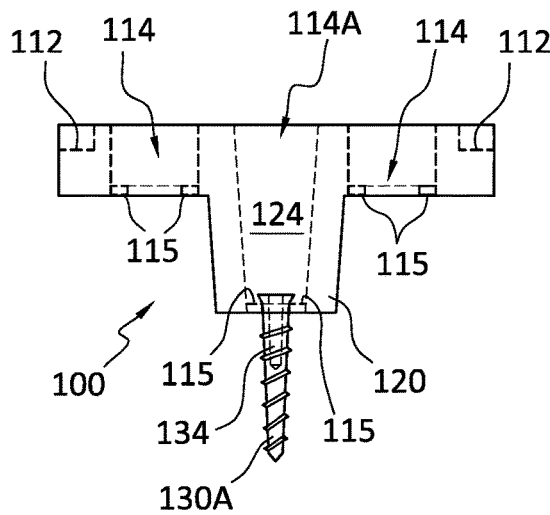

FIGS. 1A and 1B illustrate a baseplate 100 according to at least one embodiment. The illustrated baseplate 100 includes a base 110 and a stem 120 extending from the base 110. Examples of diameters for the base include between 25 mm and 30 mm and in a further example including the end points of that range. Examples of the thickness of the base 110 include between 5 mm and 15 mm (with or without the end points), 5 mm, 7 mm, 10 mm, 12.5 mm, and 15 mm. In at least one embodiment, the baseplate 100 is made from an ingrowth trabecular metal over a metal core of, for example, steel, titanium or a combination. The ingrowth trabecular metal facilitates bone ingrowth into the baseplate 100, for example to increase the strength of the connection between the bone and the baseplate 100 and the respective interface shear strength over time.

Although the stem 120 in FIG. 1B is illustrated as a cylinder with a slight taper, in at least one embodiment, the stem 120 has tapered sides to match the modular component plugs.

The illustrated base 110 includes a pair of opposed notches 112, 112 extending down from the mounting surface 111, for example on the anterior and posterior central edge (or side) of the base 110, which in at least one embodiment provides better access to the notches for removal of the modular component. In at least one embodiment, the notches 112, 112 provide a leverage point to facilitate separation of the mounted modular component from the baseplate 100 when the baseplate 100 is affixed to the glenoid. The notches 112, 112 have sufficient width and depth to receive an instrument in which to pry the mounted modular component from the baseplate 100. Although two notches 112, 112 are illustrated, additional notches could be added. In an alternative embodiment, each of the notches 112, 112 receive a flange depending from a base of the modular component, for example to increase the strength of the connection between the base 110 and the modular component 200, 300. In a further embodiment, a space will be defined by the notch 112 and the flange 212' to receive an instrument to pry the mounted modular component 200, 300 from the baseplate 100.

The illustrated base 110 includes five mounting holes 114A-114E with an axially centered hole 114A and four evenly spaced perimeter holes 114B-114E. The holes 114A-114E are illustrated as having a shoulder 115 on which a screwhead, which is an example of an attachment mechanism 130, 130A, will make contact after insertion into the baseplate 100. Although five holes are illustrated, the number of holes could be reduced or increased. In at least one embodiment, the central hole 114A defines a chamber 124 for receiving a modular component plug. In at least one embodiment, one or more variable angle locking screws 130, 130A are used to attach the baseplate 100 to the patient's glenoid bone G. FIGS. 5A and 5B illustrate the use of screws 130, 130A anchoring the baseplate 100 to the glenoid bone G. Examples of screw diameters include 4.5 mm to 5.0 mm and in a further example including the end points of that range. Although there are five holes illustrated, during a particular procedure, all five holes may not be utilized. In at least one embodiment, the flexibility in which holes 114A-114E to use and the variable angle locking screws 130, 130A provides flexibility to the orthopedic surgeon in securing the baseplate 100 to the patient's glenoid bone G. Examples of locking screw angles includes between 20 degrees and 30 degrees (with or without the end points) or perpendicular to the base 110. FIGS. 1B and 5B illustrate a screw 130A that includes a receiving cavity 134 for insertion of a torque limiting fastener inserted through the modular component.

In at least one embodiment, the central axial opening 114A passes from the base 110 into and through the stem 120 to allow for the top of the locking screw 130A to be deeper into the baseplate 100 and to provide the chamber 124' for receiving plug, e.g., the Morse taper, of the modular component being mounted onto the baseplate 100. FIG. 1C illustrates the chamber 124' having receiving screw threads for engaging a torque limiting fastener 330'. As referenced above, the torque limiting fastener may engage locking screw 130A instead or in addition to other areas of the chamber 124'. FIG. 1C illustrates the modular component as the glenosphere component 300, 300' discussed in connection with FIGS. 3A-3F.

Figure 1D:
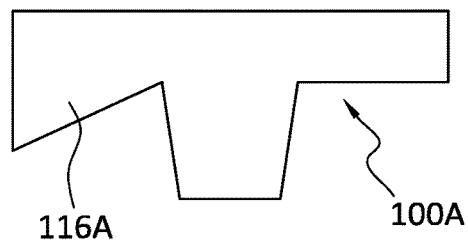
Figure 1E:
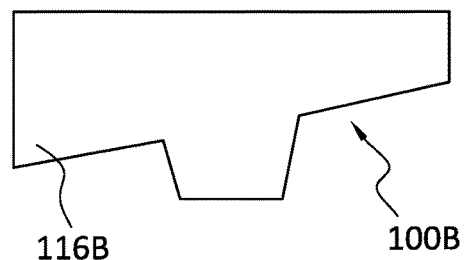

FIGS. 1D and 1E illustrate a pair of alternative baseplates 100A, 100B that have a partial wedge 116A and a full wedge 116B, respectively. One of ordinary skill in the art should appreciate that the presence of a wedge is potentially advantageous for addressing bone deformities of the glenoid while providing a secure attachment of the baseplate 100 to the patient's bone. Alternatively, the baseplate 100 can have a 10 degree or 25 degree back as oppose to the neutral back illustrated in FIG. 1B.

Figure 2A:
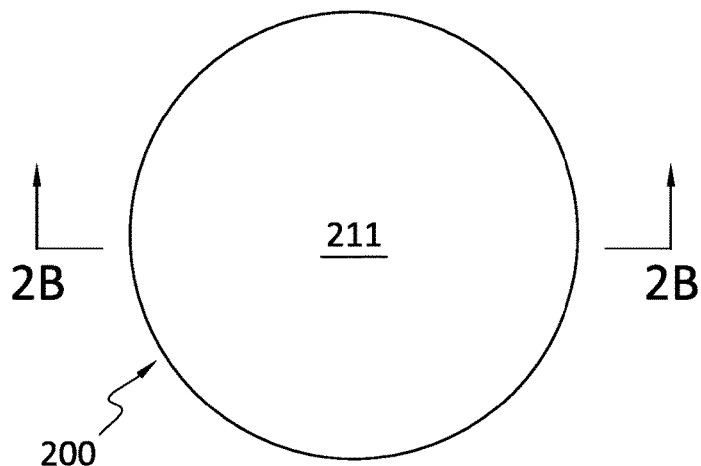
FIGS. 2A and 2B illustrate a modular glenoid component according to at least one embodiment of the invention.
Figure 2B:
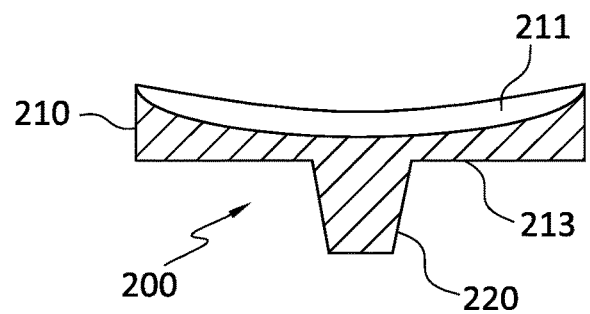

FIGS. 2A (top view) and 2B (cross-section view) illustrate a modular glenoid component 200 having a concave surface 211 on a base 210 for receiving a prosthetic ball or sphere and a plug 220 extending from a surface 213 opposed to the concave surface 211 on a base 210. One of ordinary skill in the art should appreciate based on this disclosure, the concave surface can take a variety of shapes without departing from the modularity of the modular glenoid component 200. The plug 220 is configured to be inserted and frictionally engage the chamber 124 in the baseplate 100. In at least one embodiment, the plug 220 is a Morse taper central plug.

Figure 2C:
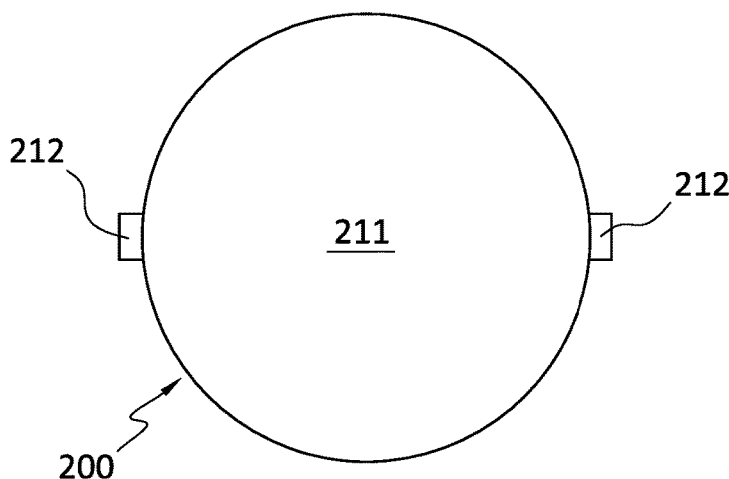
FIG. 2C illustrates a top view of an alternative modular glenoid component according to at least one embodiment of the invention.

Although the modular glenoid component 200 is illustrated as being round in FIGS. 2A and 2C, the concave surface 211 may be elliptical, oval or other similar shapes when viewed from the top.

Figure 2D:
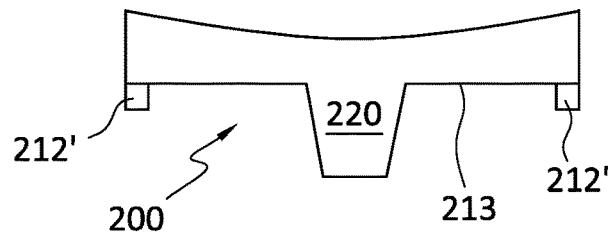
FIG. 2D illustrates a side view of another alternative modular glenoid component according to at least one embodiment of the invention.

In a further embodiment illustrated in FIG. 2C, the modular glenoid component 200 includes a pair of flanges 212, 212 extending from the anterior and posterior edges to provide additional surface area on which to apply leverage to remove the modular glenoid component 200 from the baseplate 100. In a further alternative embodiment, the flanges 212', 212' depend from the bottom surface 213 as illustrated in FIG. 2D. Flanges 212', 212' are shaped to be inserted into and engage at least a portion of a corresponding notch 112. In at least one further embodiment, the flange 212' and the notch 112 have an interference fit. As discussed above, the notch 112 and the flange 212' may define a space for receiving an instrument, or alternatively the flange 212' fully fills the space of the notch 112. In another alternative embodiment, the flanges 212, 212' illustrated in FIGS. 2C and 2D, respectively, are combined together.

In at least one embodiment, the modular glenoid component 200 is manufactured from Cobalt-Chromium (Co—Cr) to improve the life expectancy for the implant.

FIGS. 3A-3C illustrate a glenosphere component 300, 300A with a glenosphere 316 extending from a base 310 and a plug 320 extending from the base 310. In at least one embodiment, the plug 320 of the glenosphere component 300, 300A is similar to the plug 220 discussed above in connection with the modular glenoid component 200 including any further or alternative embodiments. In at least one embodiment, there is a 7-10 degree inferior tilt (see, e.g., FIGS. 3A, 3D, and 3E) added to the glenosphere that allows for improved glenosphere positioning for particular patient situations. The shape of the glenosphere may vary from that illustrated and the shape illustrated in FIGS. 3A, 3D, 3E and 5B are not intended to limit the exact shape as these are illustrative figures. More particularly, FIG. 3A illustrates a view taken anteriorly (i.e., standing in front of the shoulder when installed).

FIGS. 3B-3D illustrate an embodiment that includes a passageway 324 passing through the axial center of the glenosphere 316, 316A and the plug 320. In at least one embodiment, the passageway 324 receives a fastener (not illustrated) to further secure the modular glenoid component 300 to the baseplate 100. In a further embodiment, the passageway includes a shoulder 325 on which a screwhead will make contact after insertion into the passageway 324.

FIGS. 3B and 3C illustrate alternative embodiments for the glenosphere that both illustrate the optional passageway 324. FIG. 3B illustrates a substantially solid glenosphere 316 other than the optional passageway 324. FIG. 3C illustrates a glenosphere 316A that is hollow other than an exterior surface and the base 310A that includes the plug 320 in this embodiment. The illustrated base 310A includes a support column on which the glenosphere 316A is supported.

In a further embodiment illustrated in FIG. 3E, the modular glenoid component 300' includes a pair of flanges 312, 312 extending from the anterior and posterior edges of the glenosphere 316' to provide additional surface area on which to apply leverage to remove the modular glenoid component 300' from the baseplate 100. In a further alternative embodiment, the flanges 312', 312' depend from the glenosphere 316" when viewed from the top (or bottom) side as illustrated in FIG. 3F and similar to flanges 212', 212' discussed above in connection with the modular glenoid component 200 including alternative embodiments and hybrid flange embodiments. Based on this disclosure, it should be understood that the flanges 312, 312' may extend from the glenosphere 316 or 316A.

In a further embodiment, the glenosphere may have a surface area having an arc extending for approximately 180 degrees to approximately 270 degrees. In a further embodiment, the glenosphere is approximately a three-quarters sphere and/or hemi-spherical.

In at least one embodiment, the glenosphere 316 is made from Co—Cr.

FIGS. 4A (side view) and 4B (cross-section view) illustrate a dual-mobility humeral head 400 for a ta-TSR. The illustrated humeral head 400 includes an outer shell 419 that is pressed over an inner head 418 of a base 410 and a plug 420 for insertion into a receiving cavity 520 of a humeral stem 500 embedded into the patient's humeral bone H as illustrated in FIG. 5A. The outer shell 419 is sized to interact with the concave surface 211 of the modular glenoid component 200 as illustrated in FIG. 5A. In at least one embodiment, the inner head 418 and the outer shell 419 are hemi-spherical domes.

In at least one embodiment, the inner head 418 will be made from Co—Cr while the outer shell 419 will be made from high-density polyethylene, which will avoid the issue of having metal components rub against other metal components, which could lead to a faster wear on the components and potentially loose metal shavings within the shoulder socket.

In at least one embodiment, the humeral head 400 will have a centrally located plug 420 that is capable of being manually offset or is physically offset from the axial center to allow best coverage of the proximal humeral anatomic neck and metaphysis. The physical offset includes an eccentrically located plug 420, which when the modular humeral component is rotated provides different amounts of coverage to the humeral side.

FIG. 5A illustrates an example of how the modular humeral component, which is illustrated as the dual-mobility humeral head 400, cooperates with the modular component, which is illustrated as the modular glenoid component 200. The humeral head 400 is designed to fit into the concave surface 211 of the modular glenoid component 200, which for example is due to similar radiuses of curvature of both sides—the humeral head and the glenoid in a traditional TSR.

FIG. 5B illustrates an example of attachment of a humeral cup 600 as the modular humeral component to the humeral stem 500 while engaging with a glenosphere component 300 as the modular glenoid component to the baseplate 100. The humeral cup 600 is illustrated as having a shell 619 over a concave surface 611 (see, e.g., FIG. 6B) of the base 610 from which a plug 620 extends for engagement with the humeral stem 500. In an alternative embodiment, the glenosphere is approximately three-quarters spherical.

FIGS. 6A and 6B illustrate a humeral cup 600 for a r-TSR. The illustrated humeral cup 600 includes a concave surface (or receiving cavity) 611 on a base 610 and a plug 620 for insertion into the humeral stem 500 embedded into the patient's humeral bone H illustrated in FIGS. 5B, 7A and 7B. The concave surface 611 is adapted to interact with a glenosphere component 300. In at least one embodiment the humeral cup 600 will be made from Co—Cr, for example when the glenosphere component 300 has a high-density polyethylene cover, layer, and/or coating on it.

As illustrated in FIG. 6B, the humeral cup 600 may also have a core of Co—Cr or a similar metal to the humeral stem 500 (including a compatible metal) with a shell 619 over the concave surface 611 where the shell 619 is made from high-density polyethylene. In at least one embodiment, the polyethylene is seated into a metal concave surface 611. In an alternative embodiment, the concave surface 611 is substantially flat. In a further embodiment, the humeral cup 600' will have a shallow cylinder, for example with a height of 4 mm to 8 mm, a diameter of 30 mm, 35 mm or 40 mm to hold the various diameter humeral cup shells 619 that are inserted into a receiving cavity defined by walls 612 that extend up from the base 610' as illustrated in FIG. 7B.

In at least one embodiment, the base 610 will have a centrally located plug 620 that is capable of being manually offset or is physically offset from the axial center to allow best coverage of the proximal humeral anatomic neck and metaphysis. The physical offset includes an eccentrically located plug 620, which when the modular humeral component is rotated provides different amounts of coverage to the humeral side.

FIGS. 7A-7C illustrate an example of an alternative humeral cup 600' that may be inserted into the humeral stem 500. In at least one embodiment, the plug 620' has a Morse taper to engage the humeral stem 500. The humeral cup 600' includes a mounting base 610' and a plug 620' extending from a bottom surface of the mounting base 610'. The humeral cup 600' includes a passageway 654 passing from the bottom of the shell receiving cavity (or chamber) 613 of the mounting base 610' through the plug 620' may receive a stem of the inserted shell in a further embodiment. In at least one embodiment, the receiving cavity 611' is short with the shell fitting into the receiving cavity 611', and in a further embodiment, the shell extends beyond the top of the receiving cavity 611' away from the mounting base 610'. The passageway 654 may include a shoulder 655 around an opening to facilitate the use of an attachment mechanism as illustrated in FIGS. 7A and 7B, which opening may be omitted as illustrated in FIG. 5B. In an alternative embodiment, the passageway 654 is added to the humeral cup 600 illustrated in FIGS. 6A and 6B. In at least one embodiment, the humeral cup 600' is made of the same or compatible material of the humeral stem 500.

In at least one embodiment, the shell is press-fit into the receiving cavity 611. In at least one embodiment, the shell includes a curvature to it that has a uniform thickness, but in other embodiments the central portion is thicker than the edges. In a further embodiment, when the shell has been worn down, then it is removed and replaced. One approach for removing the shell is prying the polyethylene liner 619 from the receiving cavity 611; another approach for removing the shell is to freeze it with liquid Nitrogen to freeze and shrink it before it pops out from the receiving cavity 611.

In at least one embodiment, the stem of either humeral module is impacted onto the humeral stem such as a metaphyseal stem, short stem, or long stem through a variety of fixation techniques including, for example, a reverse Morse taper stem for the cavity 520 accepting the plug 420, 620 of the humeral head/cup 400, 600. Humeral stems known in the art with an adaptation for receiving the plug 420, 620 of the humeral head/cup 400/600 may be used. FIGS. 5A and 5B illustrate an example of a humeral stem 500 anchored in a humeral bone H.

Although particular materials have been identified for particular components and structural elements, one of ordinary skill in the art will appreciate that other materials may be substituted without departing from the scope of the invention. In at least one embodiment, modules attached to the humeral side and the glenoid side will not both be the same material at the point of interaction.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention.

As used above "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the embodiments described above can be configured without departing from the scope and spirit of the invention. Therefore, it is to be understood that, within the scope of the appended claims, the invention may be practiced other than as specifically described herein.

The invention claimed is:

1. A modular shoulder prosthesis system comprising:
   a baseplate having
      a base with a plurality of attachment holes passing therethrough and a pair of notches on opposed outer circumferential sides of said base, said pair of notches extend down from a mounting surface and in from said outer circumferential sides of said base, and
      a central stem extending from said base and axially centered with one of said plurality of attachment holes;
   a modular component configured to be removably attached to said base, said modular component having a plug for insertion into at least one attachment hole of said base;
   a humeral stem having a receiving cavity extending in from one face; and
   a modular humeral component configured to cooperate with said modular component, said modular humeral component having a post configured for removable insertion into the receiving cavity of said humeral stem, and
   wherein said baseplate is capable of attachment to different modular components and said humeral stem is capable of attachment to different modular humeral components to facilitate both traditional anatomic total shoulder replacement and reverse total shoulder replacement with a change in the modular component and change in the modular humeral component; and
   said notches are configured to provide a leverage point to facilitate separation of any attached modular component from said baseplate.

2. The system according to claim 1, wherein said modular component includes a pair of flanges extending from opposing sides of said modular component, said flanges configured to align with said notches when said modular component is attached to said base and/or configured to engage with an interference fit said notches when said modular component is attached to said base, and
   said flanges configured to provide a second leverage point on which to apply leverage for removal of said modular component after installation onto said baseplate.

3. The system according to claim 1, wherein said modular component includes
   a base having a concave surface, and
   said plug extends from a surface opposite of said concave surface.

4. The system according to claim 3, wherein said base of said modular component includes a high-density polyethylene.

5. The system according to claim 1, wherein said modular humeral component further includes
   a base having a receiving cavity,
   said plug extends from a surface opposite of said receiving cavity, and
   a shell inserted into said receiving cavity.

6. The system according to claim 5, wherein said base of said modular component includes Cobalt-Chromium and said shell includes a high-density polyethylene.

7. The system according to claim 1, wherein said modular component includes
   a base,
   a glenosphere extending from said base, and
   said plug extends from a surface of said base opposite said glenosphere.

8. The system according to claim 7, wherein said glenosphere is approximately a three-quarters sphere.

9. The system according to claim 1, wherein said modular humeral component includes
   a base having an inner head;
   an outer shell over said inner head; and
   said stem extending from said base on a surface opposing said inner head.

10. The system according to claim 9, wherein said inner head is a hemi-spherical dome and said outer shell is a hemi-spherical cap that fits over said inner head,
    said hemi-spherical cap is configured to slide relative about said hemi-spherical dome to allow for dual mobility between said hemi-spherical cap and said hemi-spherical dome.

11. The system according to claim 9, wherein said inner head includes Cobalt-Chromium and said outer shell includes a high-density polyethylene.

12. The system according to claim 1, further comprising a plurality of attachment mechanisms, wherein the attachment holes of said base of said baseplate are configured to engage with said attachment mechanisms.

13. The system according to claim 1, wherein said post of said modular humeral component is eccentrically offset or manually offsetable from an axial center of said modular humeral component.

14. A modular shoulder prosthesis system comprising:
    a baseplate having
       a base with a plurality of attachment holes passing therethrough and a pair of notches on opposed outer circumferential sides of said base, said pair of notches extend down from a mounting surface and in from said outer circumferential sides of said base, and
       a central stem extending from said base and axially centered with one of said plurality of attachment holes;
    a modular component configured to be removably attached to said base, said modular component having a plug for insertion into at least one attachment hole of said base, and
    wherein said baseplate is capable of attachment to different modular components to facilitate both traditional anatomic total shoulder replacement and reverse total shoulder replacement with a change in the modular component; and
    said notches are configured to provide a leverage point to facilitate separation of any attached modular component from said baseplate.

15. The system according to claim 14, further comprising a plurality of attachment mechanisms, wherein the attachment holes of said base of said baseplate are configured to engage with said attachment mechanisms.

16. The system according to claim 14, wherein said modular component includes a pair of flanges extending down from opposing sides of said modular component, said flanges configured to engage with an interference fit said notches when said modular component is attached to said base and to provide a second leverage point on which to apply leverage for removal of said modular component after installation onto said baseplate.

17. The system according to claim 16, wherein said modular component includes
a base having a concave surface, and
said plug extends from a surface opposite of said concave surface.

18. The system according to claim 16, wherein said modular component includes
a base,
a glenosphere extending at an angle from said base, and
said plug extends from a surface of said base opposite said glenosphere.

19. A modular shoulder prosthesis system comprising:
a first baseplate configured to attach to a glenoid, said first baseplate having
a base with a plurality of attachment holes passing therethrough and a pair of notches on opposed outer circumferential sides of said base, said pair of notches extend down from a mounting surface and in from said outer circumferential sides of said base, and
a central stem extending from said base and axially centered with one of said plurality of attachment holes;
a modular component configured to be removably attached to said base, said modular component having a plug for insertion into at least one attachment hole of said base;
a second baseplate configured to attach to a humerus, said second baseplate having a receiving cavity extending in from one face; and
a modular humeral component configured to cooperate with said modular component, said modular humeral component having a post configured for removable insertion into the receiving cavity of said second baseplate, and
wherein said first baseplate is capable of attachment to different modular components and said second baseplate is capable of attachment to different modular humeral components to facilitate both traditional anatomic total shoulder replacement and reverse total shoulder replacement with a change in the modular component and change in the modular humeral component;
said first baseplate and said second baseplate are substantially identical; and
said notches of said first baseplate are configured to provide a leverage point to facilitate separation of any attached modular component from said first baseplate.

20. The system according to claim 19, wherein said modular component includes a pair of flanges extending from opposing sides of said modular component, said flanges configured to engage with an interference fit said notches when said modular component is attached to said base, and a length of said flange is less than or equal to a height of said notch,
said second baseplate includes a base with a plurality of attachment holes passing therethrough and a pair of notches on opposed outer circumferential sides of said base, said pair of notches extend down from a mounting surface and in from said outer circumferential sides of said base, and
wherein said modular humeral component includes a pair of flanges extending from opposing sides of said modular humeral component, said flanges configured to engage with an interference fit said notches of said second baseplate when said modular humeral component is attached to said second baseplate,
said flanges of said modular component configured to provide additional surface area on which to apply leverage for removal of said modular component after installation onto said first baseplate, and
said flanges of said modular humeral component configured to provide additional surface area on which to apply leverage for removal of said modular humeral component after installation onto said second baseplate.

21. The system according to claim 9, wherein said inner head of said base and said outer shell are configured to slide relative to each other to provide dual mobility.

22. The system according to claim 14, wherein said modular component includes a pair of flanges extending from opposing sides of said modular component, said flanges configured to engage with an interference fit said notches when said modular component is attached to said base, and a length of said flange is less than or equal to a height of said notch, and
said flanges configured to provide additional surface area on which to apply leverage for removal of said modular component after installation onto said baseplate.

23. The system according to claim 14, wherein said modular component includes a pair of flanges extending radially out from opposing anterior and posterior sides of said modular component, said flanges configured to align with said notches of said baseplate when said modular component is attached to said base, and said flanges configured to provide additional surface area on which to apply leverage for removal of said modular component after installation onto said baseplate.

24. The system according to claim 14, wherein said notches are on the anterior and posterior sides of said base.

* * * * *